United States Patent
Denuell

(10) Patent No.: US 6,725,123 B1
(45) Date of Patent: Apr. 20, 2004

(54) METHOD AND APPLIANCE FOR DETECTING, IDENTIFYING AND RELOCATING DEFECTS IN A MATERIAL STRIP

(75) Inventor: Hans-Joerg Denuell, Aachen (DE)

(73) Assignee: Parsytec Computer GmbH, Aachen (DE)

( * ) Notice: Subject to any disclaimer, the term of this patent is extended or adjusted under 35 U.S.C. 154(b) by 0 days.

(21) Appl. No.: 09/506,400

(22) Filed: Feb. 18, 2000

(30) Foreign Application Priority Data

Feb. 18, 2000 (DE) .......................... 199 06 701

(51) Int. Cl.[7] .............................................. G06F 19/00
(52) U.S. Cl. ...................... 700/122; 101/219; 250/548; 702/35
(58) Field of Search .............................. 700/108, 109, 700/122, 110, 127; 702/35, 36; 250/548; 101/213, 219, 272, 223

(56) References Cited

U.S. PATENT DOCUMENTS

| | | | |
|---|---|---|---|
| 3,500,437 A | * 3/1970 | Foerster | 346/106 |
| 4,286,880 A | * 9/1981 | Young | 356/431 |
| 4,417,149 A | * 11/1983 | Takeuchi et al. | 250/559.46 |
| 4,746,020 A | 5/1988 | Schenk | 209/3.3 |
| 4,865,872 A | * 9/1989 | Pellatiro | 427/9 |
| 4,972,326 A | 11/1990 | Jung et al. | 702/36 |
| 5,187,376 A | * 2/1993 | Hashimoto et al. | 250/559.02 |
| 5,949,550 A | * 9/1999 | Arndt et al. | 356/430 |
| 6,299,730 B1 | * 10/2001 | Broek et al. | 162/198 |

FOREIGN PATENT DOCUMENTS

| | | |
|---|---|---|
| DE | 33 25 125 | 2/1985 |
| EP | 0 303 722 | 2/1989 |

* cited by examiner

*Primary Examiner*—Leo Picard
*Assistant Examiner*—Chad Rapp
(74) *Attorney, Agent, or Firm*—Foley & Lardner LLP

(57) ABSTRACT

The invention relates to a device and a method for detecting, identifying and relocating defects in a material strip of great length. In order to enable defects to be relocated reliably and quickly with relatively little effort, the material strip is checked for defects, and position indicators are applied to the material strip continuously over its length. In the event of a defect being observed, an associated defect position indicator is stored, and during the subsequent relocation of a defect, a current starting position indicator is established, and the material strip is moved over a conveying length which is calculated from the established starting position indicator and the stored defect position indicator.

20 Claims, 1 Drawing Sheet

METHOD AND APPLIANCE FOR DETECTING, IDENTIFYING AND RELOCATING DEFECTS IN A MATERIAL STRIP

BACKGROUND OF THE INVENTION

1. Field of the Invention

The invention relates to a method and an appliance for detecting, identifying and relocating defects in a material strip of great length.

2. Description of the Related Art

During the production of paper, steel and plastics, for example, the material produced is released from the manufacturing machines in great lengths. In endless processes of this nature, the strip material produced is generally examined by an optical inspection system to search for flaws or defects, such as for example, surface defects. If a defect is discovered, the material strip which is coming out of the manufacturing machine cannot generally be stopped in order for an area of material containing the defects to be cut out, since the production operation is not to be interrupted. Consequently, in the event of a defect being detected, the corresponding location on the material strip is merely marked, so that this location can be relocated subsequently. To unload the manufacturing machine, the material strip is collected in relatively large quantities, for example, by being wound up into reels of material. After a relatively large amount of material has been collected, the material strip is severed, and the collected material strip is removed, for example, as a reel.

When the strip is subsequently reversed, for example, by being rewound, these marked locations can then be approached again, rechecked and, if appropriate, cut out. The marked locations are generally approached manually, to ensure that no marks are overlooked.

However, in the case of long strips, manually approaching the marked locations is very time-consuming and laborious. The material strip has to be unwound at a medium speed and has to be checked by an operator for possible marks. Although in principle it is possible for the reels of material strip collected during unloading to be provided with corresponding identifiers in order to indicate the presence and the position indicator of defects, since the reels of material strip are generally of different lengths, since they may be larger or smaller according to the production operation requirements and, in particular, in some cases pieces of undefined length have already been cut off the strip prior to the rewinding, in order to take specimens or remove irregular areas at the end of the material strip, such markings are insufficient to enable the position of the defects to be accurately determined. Consequently, it is currently necessary for the strip material to be manually unwound with care and checked for possible marks.

EP 0 303 722 A1 reveals a method and device for recording and treating defects in webs of material, in which a defect is registered by its position in an X-direction being recorded by a mark placed on the web of material and by at least one further position indicator being recorded together with an identification of the mark being recorded. Further position indicators determined and stored are X-Y-coordinates of a family of points which fix a boundary line around the defect, the mark or a side edge of the material web serving as a reference point for these X- and Y-coordinates.

DE 33 15 125 C1 has disclosed an arrangement for marking defect locations on webs of material, in which the web of material is guided past a defect-recording scanning device and a marking device which is at a distance therefrom. Signals from the defect-recording scanning device are successively analyzed to check whether they are defect or structure signals, the defect signals determined being stored together with their coordinates on the web. At intervals, it is checked whether there is a defect signal in the memory concerning the longitudinal coordinate which is in the process of moving past the marking device, and if such a signal is present a marking is made at the corresponding coordinates on the web.

SUMMARY OF THE INVENTION

The primary objects of the invention reside in providing a method and a device for detecting, identifying and relocating defects in a material strip of great length, in which detected defects can be relocated reliably and quickly with relatively little effort.

According to one aspect of the invention, there is provided a method in which a material strip is checked for defects, and position indicators are applied to the material strip continuously over its length. In the event of a defect being observed, an associated defect position indicator is stored, and during the subsequent relocation of a surface defect, a current starting position indicator is established and the material strip is moved over a conveying length which is calculated from the established starting position indicator and the stored defect position indicator.

The invention furthermore provides a device comprising an optical inspection device for observing a defect, a marking device for marking the material strip, whereby position indicators can be applied continuously to the material strip, and a memory device whereby measurement data from the optical inspection device can be recorded and can be stored together with the associated position indicator.

Further objects, features and advantages of the invention will become apparent from the detailed description of preferred embodiments that follows when considered together with the accompanying figures of drawing.

BRIEF DESCRIPTION OF THE DRAWINGS

The invention is explained in more detail below with reference to the appended drawings, in which.

DETAILED DESCRIPTION OF THE PREFERRED EMBODIMENT

Figure 1:
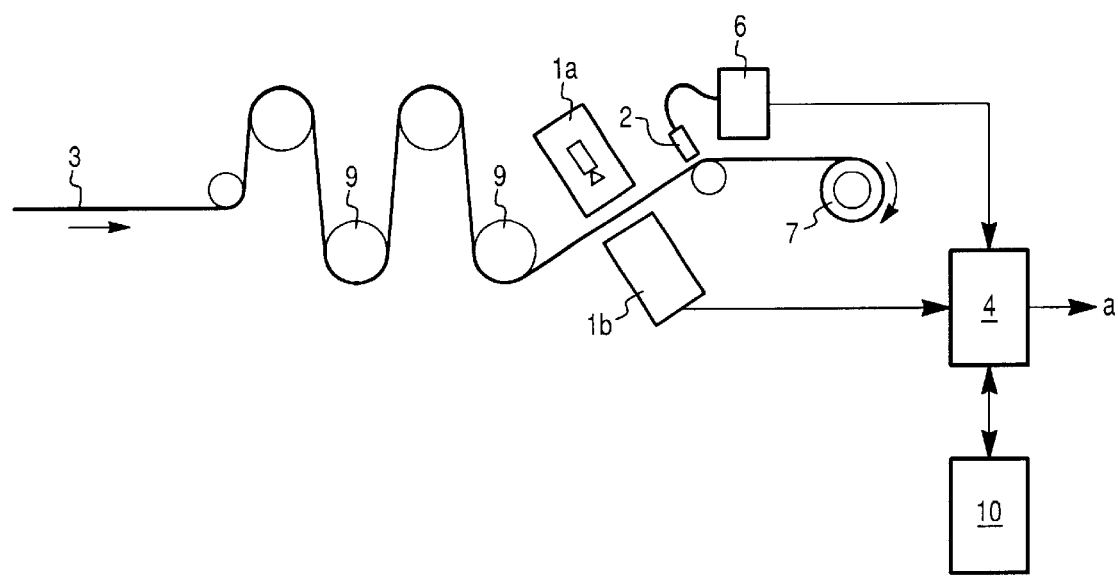
FIG. 1 is a schematic representation of a first step of a method according to the invention during unloading of a manufacturing machine.

The invention provides a method for detecting, identifying and relocating defects in a material strip of great length, in which the material strip is checked for defects, and position indicators are applied to the material strip continuously over its length. In the event of a defect being observed, an associated defect position indicator is stored, and during the subsequent relocation of a defect, a current starting position indicator is established, and the material strip is moved over a conveying length which is calculated from the established starting position indicator and the stored defect position indicator.

The invention also provides a device for detecting, identifying and relocating a defect in a material strip of great length, in particular for carrying out the method as defined above, comprising an optical inspection device for observing a defect, a marking device for marking the material strip, by means of which position indicators can be applied continuously to the material strip, and a memory device, by means of which defect measurement data from the optical inspection device can be recorded and can be stored together with the associated position indicator.

According to the invention, therefore, markings are also applied to the material strip, in order for the detected surface defects to be relocated subsequently. For this purpose, however, position indicators are also applied to the strip continuously, so that the marking is independent of the defect detection. The determination of the position indicators may, for example, be carried out by measuring the strip length or, given a constant strip speed, by means of a simple counting device. In the event of a defect being discovered, the current position indicator can be stored as a defect position indicator without a special imprint on the strip being required for this purpose. Since position indicators are applied continuously to the material strip, a conveying length can be determined during the subsequent relocation, for example, during a rewinding operation, on the basis of a final position indicator on the strip material and the stored defect position indicator. In the simplest case, the conveying length can be determined directly as the difference between the final position indicator and the stored defect position indicator.

When relocating and removing a defect, all the material around the defect detected is generally removed, so that there is no need for a very accurate position indicator, for example, in the millimeter or centimeter range, on the material strip. Consequently, the defect can be relocated simply using markings within relatively large length indicators, so that, on the one hand, the costs of marking, such as for example, costs incurred through printing ink and wear to the material of the printer, can be lowered and, on the other hand, the unloading speed is not limited by the marking device. A relatively large scale, which may, for example, lie in the decimeter or meter range, is sufficient for the position indicator. A scale providing position indicators at intervals of several meters, for example every 10 m, or even greater length intervals, is also possible.

The method according to the invention can be automated in particular because only one starting position indicator has to be input to a control device when relocating the defect. The control device uses the stored defect position indicator to automatically calculate a rewinding length and moves the material strip in the reverse direction by the desired length through controlling a rewinding device. Since the position imprint is made independently of the detection of the defects, it is possible to dispense with real-time conditions during the defect analysis and defect evaluation. This allows more thorough analysis and automatic classification of the defects. Such classification can also be used in particular to relocate the defects selectively, according to the severity or nature of the defect. For relocation purposes, a control device can advantageously unwind the strip material at a high unwinding speed to a prewinding distance before the defect location and can then unwind the strip at a lower speed, so that the operating staff can accurately locate and assess the defect. Furthermore, the strip can be stopped automatically when the calculated defect position is reached, so that the operating staff do not have to carry out a stopping operation of this nature. In principle, however, manual stopping is also possible, in addition to or instead of this automated stopping.

Turning now to the drawings, a material strip 3, which may consist, for example, of paper, steel or a plastic material, is output as an endless strip from a manufacturing machine and is picked up by guide rollers 9 as shown in FIG. 1. Then, an optical inspection device 1a, 1b is used to check for damaging defects, such as for example, surface defects. The optical inspection device as shown in FIG. 1 may have a projection device 1a and a sensor device 1b, by means of which surface defects are recognized as changes in the strip material. The material strip 3 is then guided past the print head 2 of a printing unit 6 and wound up into a material reel 7.

According to the invention, the printing unit 6 uses the print head 2 to print position indicators continuously on the material strip. The position indicators may in particular be applied to one edge, both edges or the rear side of the material in question. The printing is preferably produced by means of ink. The position indicators may be arranged at intervals of, for example, decimeters, one or more meters, such as for example, every 10 meters, and may either represent continuous numbers or may directly indicate a length since the beginning of winding. The printing unit may also be controlled, for example, by a control device of the material reel 7, which controls and/or measures the speed at which the material reel 7 is wound. The printed position indicators are transmitted from the printing unit 6 to a control device 4. The control device 4 also records defect data from the sensor device 1b, so that in the event of a defect, such as for example, a surface defect, being discovered, mutually associated values can be recorded by the memory unit 4. The control device 4 stores the position indicator data and the defect data in a memory device 10 which may also, for example, be an internal memory device of the control device 4. The control device 4 can in this case initially assess the data transmitted from the sensor device 1b and then, on the basis of the sensor data, establish what type of defect has been detected. In particular, it can determine the nature and the seriousness of such a defect. After the nature of the defect has been established, an indication of the nature of the defect is stored in the memory device 10 together with the position indicator transmitted from the printing unit 6 at this time. During subsequent rewinding, the control device can retrieve this stored data from the memory device 10 and transmit it, as indicated by the arrow a, to a rewinding control device 8, which is shown in FIG. 2.

Figure 2:
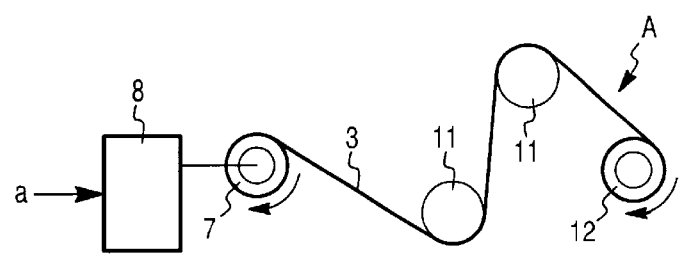
FIG. 2 is a schematic representation of a second step of a method according to the invention during relocation of a detected defect.

As shown in FIG. 2, for unwinding purposes, the data stored in the memory device 10 is transmitted via the winding control device 4 to the rewinding control device 8. A starting position indicator is established at the end of the first material reel 7. This starting position indicator may correspond to the last position indicator that was printed on the material strip 3 before the strip material was severed and the material reel 7 was changed. However, since strip pieces of undefined length may have been cut off from the web after the end of the winding operation, it is also possible to use a different value. After the starting position indicator on the material strip 3 has been read and input into the rewinding control system 8, the control device uses the defect position indicators and the input starting position indicator to calculate the rewinding length by which the material strip has to be rewound in order to reach a damaged location. The first material reel 7 and a second material reel 12 are then driven suitably by the rewinding control system 8, in such a manner that the material strip 3 is displaced over guide rollers 11 sufficiently far for it to be possible for an observer to see the next defect or a desired defect from the location indicated by A, in the direction of the arrow. For this purpose, the material strip 3 can initially be moved quickly, and then slowly just before the desired location is reached, and then stopped when the defect position is reached. The observer can then see the defect and cut out a length of strip around the defect from the material strip 3, if necessary or desirable.

It will be apparent to persons of ordinary skill in the art that other alternative embodiments are possible for realizing the present invention. It is intended to encompass and protect all such modifications and alternative embodiments by means of the appended claims.

The entire content of German Patent Application No. 199 06 701.5 is hereby incorporated by reference.

I claim:

1. A method for detecting, identifying and relocating defects in a material strip of great length, comprising:
    moving the material strip;
    checking the material strip for defects while the material strip is moving,
    applying position indicators to the material strip continuously over its length,
    in an event of a possible defect being observed, storing an associated defect position indicator; and
    during a subsequent relocation of a defect, establishing a current starting position indicator and moving the material strip over a conveying length which is calculated from the established starting position indicator and the stored defect position indicator.

2. A method as claimed in claim 1, wherein the position indicators are applied to at least one of one edge, both edges and a rear side of the material strip.

3. A method as claimed in claim 1, wherein the position indicators are printed onto the material strip.

4. A method as claimed in claim 1, wherein the starting position indicator established for relocation of the defect is at one end of the material strip.

5. A method as claimed in claim 1, wherein the conveying length for relocation of a defect is calculated from a difference between the current starting position indicator and the defect position indicator.

6. A method as claimed in claim 1, further comprising storing data concerning a nature of an observed possible defect and at a time subsequent to the checking for defects evaluating the stored data to determine whether there is an actual defect.

7. A method as claimed in claim 6, wherein the checking for defects and the application of the position indicators are carried out independently of one another.

8. A method as claimed in claim 1, wherein the material strip is checked for surface defects.

9. A method as claimed in claim 1, wherein, when a possible defect is observed, a distinction is drawn according to a nature of the defect, and data concerning the nature of the defect are stored together with the defect position indicator.

10. A method as claimed in claim 9, wherein, during relocation, the possible defects, are considered according to the stored data concerning the nature of the possible defect.

11. A method as claimed in claim 1, wherein the relocation of the defect or defects is carried out while the material strip is being rewound.

12. A method as claimed in claim 11, wherein a rewinding speed for relocation of the defects is selectively adjusted based on the position indicators on the material strip.

13. A device for detecting, identifying and relocating a defect in a material strip of great length, comprising:
    a moving device for moving the material strip;
    an optical inspection device for observing a possible defect on the material strip while the material strip is moving;
    a marking device for continuously applying position indicators to the material strip; and
    a memory device, for storing defect measurement data from the optical inspection device together with an associated position indicator for the observed possible defect.

14. A device as claimed in claim 13, wherein the marking device comprises a printing unit.

15. A device as claimed in claim 14, wherein the printing unit is configured to print position indicators onto at least one of a single edge, both edges and a rear side of the material strip.

16. A device as claimed in claim 13, further comprising a rewinding device and a rewinding control device connected to the rewinding device and wherein the memory device is connected to the rewinding control device for controlling the rewinding device as a function of established starting position indicators prior to a commencement of a rewinding operation and stored defect position indicators.

17. The device as claimed in claim 13, wherein the moving device comprises a reel onto which the material strip is wound without interruption.

18. The method as claimed in claim 1, wherein the step of moving the material strip comprises winding the material strip onto a reel without interruption.

19. A device for detecting, identifying and relocating a defect in a material strip of great length, comprising:
    a moving means for moving the material strip;
    an optical inspection means for observing a possible defect on the material strip while the material strip is moving;
    a marking means for continuously applying position indicators to the material strip; and
    a memory means for storing defect measurement data from the optical inspection means together with an associated position indicator for the observed possible defect.

20. A device as claimed in claim 19, further comprising a rewinding device and a rewinding control device connected to the rewinding device and wherein the memory means is connected to the rewinding control device for controlling the rewinding device as a function of established starting position indicators prior to a commencement of a rewinding operation and stored defect position indicators.

* * * * *

UNITED STATES PATENT AND TRADEMARK OFFICE
CERTIFICATE OF CORRECTION

PATENT NO. : 6,725,123 B1
DATED : April 20, 2004
INVENTOR(S) : Hans-Joerg Denuell It is certified that error appears in the above-identified patent and that said Letters Patent is hereby corrected as shown below:

Title page,
Item [30], Foreign Application Priority Data, should read:
-- February 18, 1999    (DE)    199 06 701.5 --

Signed and Sealed this

Twenty-ninth Day of June, 2004

JON W. DUDAS
*Acting Director of the United States Patent and Trademark Office*